United States Patent
Ignatious

(10) Patent No.: US 7,205,378 B2
(45) Date of Patent: Apr. 17, 2007

(54) LACTONE BEARING ABSORBABLE POLYMERS

(75) Inventor: Francis X. Ignatious, Exton, PA (US)

(73) Assignee: Societe de Conseils de Recherches et d'Applications Scientifiques, SAS, Paris (FR)

( * ) Notice: Subject to any disclaimer, the term of this patent is extended or adjusted under 35 U.S.C. 154(b) by 0 days.

(21) Appl. No.: 11/114,452

(22) Filed: Apr. 26, 2005

(65) Prior Publication Data

US 2005/0267280 A1 Dec. 1, 2005

Related U.S. Application Data

(60) Division of application No. 09/830,945, filed as application No. PCT/US99/25706 on Nov. 2, 1999, now Pat. No. 6,955,822, which is a continuation of application No. 09/184,413, filed on Nov. 2, 1998, now abandoned.

(60) Provisional application No. 60/106,708, filed on Nov. 2, 1998.

(51) Int. Cl.
 *C08G 64/00* (2006.01)
(52) U.S. Cl. .................. 528/272; 215/11.1; 428/35.7; 514/212.01; 514/212.02; 528/354
(58) Field of Classification Search ............. 215/11.1; 428/35.7; 514/212.01, 212.02; 528/354, 528/272
 See application file for complete search history.

(56) References Cited

U.S. PATENT DOCUMENTS

| 4,675,189 A | 6/1987 | Kent et al. |
| 4,767,628 A | 8/1988 | Hutchinson |
| 4,943,382 A * | 7/1990 | Gutierrez et al. ........... 508/291 |
| 5,256,765 A | 10/1993 | Leong |

FOREIGN PATENT DOCUMENTS

| EP | 0 440 108 | 8/1991 |
| GB | 2 145 422 A | 3/1985 |
| WO | WO 93/20126 | 10/1993 |

OTHER PUBLICATIONS

Hashimoto, K. et al., "Macromolecular Synthesis from Saccharic Lactones . . . ", J. of Poly. Science: Part A: Polymer Chem., vol. 33, pp. 1495-1503, (1995).
Hutchinson, F.G. et al., "Biodegradable Polymer Systems for the Sustained Release of PolyPeptides", J. of Controlled Release, vol. 13, pp. 279-294, (1990).
Johns, D. B. et al., "Lactones", Ring-Opening Polymerization, vol. 1, Chapter 7, pp. 461-521, edited by K. J. Ivin & T. Saegusa, Elsevier Applied Science Publishers, London & New York, (1984).
O'Donnell, P.B. et al., "Preparation of Microspheres by the Solvent Evaporation Technique", Adv. Drug Delivery Reviews, vol. 28, pp. 25-42, (1997).
Sintzel, M. B. et al., "Synthesis and Characterization of Self-Catalyzed poly(ortho ester)", Biomaterials, vol. 19, pp. 791-800, (1998).
Vandorpe, J. et al., "Biodegradable Polyphosphazeres for Biomedical Applications", Handbook of Biodegradable Polymers, pp. 161-182, Chapter 9, edited by A. J. Domb, J. Kost and D. M. Wiseman, Harwood Academic Publishers, Australia et al., (1997).

* cited by examiner

*Primary Examiner*—Terressa Boykin
(74) *Attorney, Agent, or Firm*—Fish & Richardson; Alan F. Feeney; Tony K. Uhm

(57) ABSTRACT

The present invention pertains to biodegradable polymers comprising a non-polymerizable lactone, biodegradable compositions comprising the polymer and a therapeutic agent, the use of the compositions for the sustained release of therapeutic agents, wherein the therapeutic agent is reversibly immobilized on the polymer matrix using ionic complexation between the latent carboxylic groups present on the lactone bearing polymer matrix and a cationic group on the therapeutic agent.

17 Claims, No Drawings

LACTONE BEARING ABSORBABLE POLYMERS

This application is a divisional application of U.S. application Ser. No. 09/830,945, filed Jul. 12, 2001 now U.S. Pat. No. 6,955,822, which is a national phase application filed under 35 U.S.C. 371 of International Application No. PCT/US99/25706, filed Nov. 2, 1999, which claims benefit of U.S. application Ser. No. 09/184,413, filed Nov. 2, 1998 now abandoned, and U.S. Provisional Application No. 60/106,708, filed Nov. 2, 1998, which is incorporated herein by reference in its entirety.

BACKGROUND OF THE INVENTION

The present invention pertains to biodegradable polymers comprising a lactone, biodegradable compositions comprising the polymer and a therapeutic agent, the use of the compositions for the sustained release of therapeutic agents, wherein the therapeutic agent is reversibly immobilized on the polymer matrix using ionic complexation between the latent carboxylic groups present on the lactone bearing polymer matrix and the cationic group on the therapeutic agent.

In order to overcome the multiple dosing regime associated with therapy involving therapeutic agents, which includes peptides and proteins, having a short in vivo half life, numerous technologies are being evaluated for the sustained release of these therapeutic agents. One of these technologies is the encapsulation of drugs in biodegradable matrices such as polyesters, polycarbonates, polyanhydrides, polyorthoesters, polyphosphazenes, polyphosphoesters and the like (see U.S. Pat. No. 4,675,189; U.S. Pat. No. 4,767,628; U.S. Pat. No. 5,271,945; WO 93/20126; GB Patent No. 2,145,422). The biodegradable microparticles containing the therapeutic agent(s) slowly release to maintain an effective plasma level for several days or even for months. The release of the therapeutic agent is dictated by a variety of factors arising from the polymer matrix as well as the physical characteristics of the therapeutic agent, making it possible to engineer the release profile by properly selecting the parameters governing them. The biodegradable polymer matrix degrades in vivo to non-toxic metabolites, at rates depending on the chemical nature of the polymer.

However, one of the many problems, encountered during the encapsulation of therapeutic agents in such biodegradable matrices is the inherent incompatibility between the polymer matrix and the therapeutic agent, such as a polypeptide. This incompatibility often leads to poor encapsulation efficiency as manifested during the emulsion solvent evaporation process, described by the oil-in-water process (P. B. O'Donnell and J. W. McGinity in Advanced Drug Delivery Reviews, 28(1997), 25–42.). Another consequence of the incompatibility between the polymer matrix and a therapeutic agent, is the formation of phase separated domains inside the microparticle. The release of a therapeutic agent from such a phase separated, non-homogenous system becomes non-predictable. One of the ways to overcome such incompatibility is to anchor the therapeutic agent onto a polymer matrix using reversible bonds such as ionic bonds. These ionic complexes are formed between carboxylic functionalities of the polyester and cationic groups of the therapeutic agent as described in the U.S. Pat. No. 5,672,659. The carboxylic acid functionalized polyesters were obtained by the ring opening polymerization of lactones using hydroxycarboxylic acid as an 'initiator', whereby the molecular weight of the resulting polyester is controlled by the molar ratio of the hydroxycarboxylic acid with respect to the monomers. The hydroxy group present in the hydroxycarboxylic acid is expected to participate in the ring opening polymerization, producing telechelic polymers having hydroxy and carboxylic groups at the chain extremities. However, the presence of carboxylic group in the initiator can interfere with the polymerization, as discussed by Zhang et al, in Journal Polymer Science, Polymer Chemistry Ed. 1994, 32,2965.

In this context the teachings of the present invention become relevant. Five membered ring lactones and certain six membered lactones (see review by Johns, D. H. et al., in Ring Opening Polymerization, edited by K. J. Ivin and T. Saegusa, Elsevier Applied Science Publishers, N.Y.) are thermodynamically stable and are considered non-polymerizable under the normal conditions of polymerization described by the present invention. An active hydrogen present on a five membered ring lactone, can be used to initiate the polymerization of other lactones, without affecting the five membered ring lactone. Therefore the five membered ring lactones can be incorporated intact, without unfavorably affecting the polymerization as would have been the case when hydroxy carboxylic acids are used as the initiator. These five membered ring lactones can be selectively used to anchor a therapeutic agent such as a polypeptide either by ionic complexation or by covalent conjugation.

Hashimoto et al., describe the synthesis of polyurethanes containing glucarodilactones and mannarodilactones by the reaction between the dihydroxy groups present on the dilactone with diisocyanates (Journal of Polymer Science: Part A, Polymer Chemistry 1995, 33, 1495). However, such monomers have never been used in the synthesis of polyesters, polyorthoesters, polyphosphazenes, polycarbonates, polyanhydrides, polyphosphoesters, and the like.

SUMMARY OF THE INVENTION

In one aspect, the present invention is directed to a polymer bearing non-polymerizable lactone ring wherein the polymer is selected from the group consisting of polyester, polyorthoester, polyphosphoester, polycarbonates, polyanhydrides and polyphosphazenes and copolymers and blends thereof. Depending on the lactone ring starting material that is used to make the polymer bearing non-polymerizable lactone ring, there may be one or multiple lactone rings in the polymer bearing non-polymerizable lactone ring. This is described in more detail below.

The polymer bearing non-polymerizable lactone ring described immediately above can have the non-polymerizable lactone within the polymer chain or the non-polymerizable lactone can be bonded to one or both ends of the polymer chain.

A preferred polymer bearing non-polymerizable lactone ring is where the polymer is a polyester. A preferred embodiment of the immediately foregoing polymer is where the polyester is selected from the group consisting of polymers, copolymers or blends of l-lactide, di-lactide, d-lactide, lactic acid, ε-caprolactone, hydroxycaproic acid, p-dioxanone, trimethylene carbonate, 1,5-dioxepan-2-one, 1-4 dioxepan-2-one, glycolide, glycolic acid, ethylene glycol, propylene glycol valerolactone, hydroxyvaleric acid, and butanediol. More preferred is where the polyester is selected from the group consisting of l-lactide, dl-lactide, glycolide, and polyethylene glycol and the non-polymerizable lactone ring is selected from the group consisting of hydroxybutyrolactone, erythrynolactone, isopropylidene ribonolactone, isocitric acid lactone, mannarolactone, sacharrodilactone and glucarodilactone.

Another preferred polymer bearing non-polymerizable lactone ring is where the polymer is a polyorthoester. A preferred embodiment of the immediately foregoing polymer is where the polyorthoester is obtained from a diketene acetal and a dihydroxy non-polymerizable lactone bearing prepolymer. A preferred embodiment of the immediately foregoing polymer is where the dihydroxy non-polymerizable lactone bearing prepolymer comprises a polyester selected from the group consisting of polymers, copolymers or blends of l-lactide, dl-lactide, lactic acid, ε-caprolactone, hydroxycaproic acid, p-dioxanone, trimethylene carbonate, 1,5-dioxepan-2-one, 1-4 dioxepan-2-one, glycolide, glycolic acid, ethylene glycol, propylene glycol valerolactone, hydroxyvaleric acid, and butanediol.

Another preferred polymer bearing non-polymerizable lactone ring is where the polymer is a polyphosphoester. A preferred embodiment of the immediately foregoing polymer is where the polyphosphoester is obtained from ($C_1$–$C_{18}$)alkylphospho-dichloridates, cycloalkylphosphodichloridates or arylphosphodichloridates and a dihydroxy non-polymerizable lactone bearing prepolymer. A preferred embodiment of the immediately foregoing polymer is where the dihydroxy non-polymerizable lactone bearing prepolymer comprises a polyester selected from the group consisting of polymers, copolymers or blends of l-lactide, dl-lactide, lactic acid, ε-caprolactone, hydroxycaproic acid, p-dioxanone, trimethylene carbonate, 1,5-dioxepan-2-one, 1-4 dioxepan-2-one, glycolide, glycolic acid, ethylene glycol, propylene glycol valerolactone, hydroxyvaleric acid, and butanediol.

Another preferred polymer bearing non-polymerizable lactone ring is where the polymer is a polycarbonate.

Another preferred polymer bearing non-polymerizable lactone ring is where the polymer is a polyanhydride.

Another preferred polymer bearing non-polymerizable lactone ring is where the polymer is a polyphosphazene. A preferred embodiment of the immediately foregoing polymer is where the polyphosphazene is obtained from poly(dichloro)phosphazene and amino butyrolactone.

In another aspect, the present invention is directed to a polymer bearing non-polymerizable lactone ring where the polymer is a polyester and wherein the non-polymerizable lactone has been ring opened to its corresponding hydroxycarboxylic acid alkali metal salt. For example, the following scheme shows a polymer bearing a non-polymerizable lactone bearing ring of the present invention before and after ring opening of the lactone ring, it is the ring opened product which is the object of this aspect of the present invention.

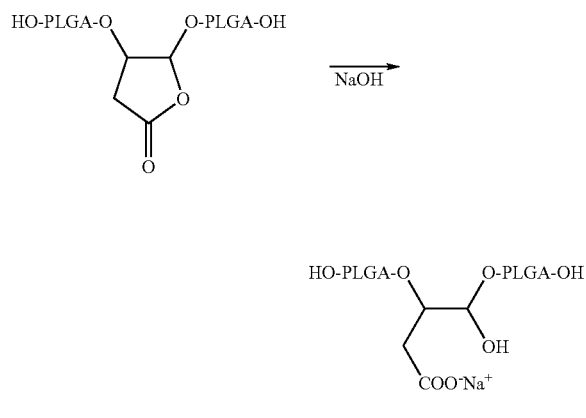

A preferred embodiment of the immediately foregoing polymer is where the polyester is selected from the group consisting of polymers, copolymers or blends of l-lactide, dl-lactide, d-lactide, lactic acid, ε-caprolactone, hydroxycaproic acid, p-dioxanone, trimethylene carbonate, 1,5-dioxepan-2-one, 1-4 dioxepan-2-one, glycolide, glycolic acid, ethylene glycol, propylene glycol valerolactone, hydroxyvaleric acid, and butanediol. More preferred is when the polyester is selected from the group consisting of l-lactide, dl-lactide, glycolide, and polyethylene glycol and the hydroxycarboxylic acid corresponds to the ring opened product of the non-polymerizable lactone ring selected from the group consisting of hydroxybutyrolactone, erythrynolactone, isopropylidene ribonolactone, isocitric acid lactone, mannarolactone, sacharrodilactone and glucarodilactone. A most preferred embodiment of the foregoing polymer is where the hydroxycarboxylic acid alkali metal salt is within the polymer chain.

In yet another aspect, the present invention provides a complex comprising a polymer bearing non-polymerizable lactone ring, ionically complexed with a therapeutic agent containing at least one cationic group, wherein the polymer is selected from the group consisting of polyester, polyorthoester, polyphosphoester, polycarbonates, polyanhydrides and polyphosphazenes, and copolymers and blends thereof. A preferred embodiment of the foregoing complex is where the polymer part of the polymer bearing non-polymerizable lactone ring is a polyester and wherein the non-polymerizable lactone ring has been ring opened to its corresponding hydroxycarboxylic acid alkali metal salt, is ionically complexed with a therapeutic agent containing at least one cationic group. A preferred embodiment of the immediately foregoing polymer is where the polyester is selected from the group consisting of polymers, copolymers or blends of l-lactide, dl-lactide, d-lactide, lactic acid, ε-caprolactone, hydroxycaproic acid, p-dioxanone, trimethylene carbonate, 1,5-dioxepan-2-one, 1-4 dioxepan-2-one, glycolide, glycolic acid, ethylene glycol, propylene glycol valerolactone, hydroxyvaleric acid, and butanediol. More preferred is where the polyester is selected from the group consisting of l-lactide, dl-lactide, glycolide, and polyethylene glycol and the hydroxycarboxylic acid corresponds to the ring opened product of the non-polymerizable lactone ring selected from the group consisting of hydroxybutyrolactone, erythrynolactone, isopropylidene ribonolactone, isocitric acid lactone, mannarolactone, sacharrodilactone and glucarodilactone. A most preferred embodiment of the foregoing polymer is where the hydroxycarboxylic acid alkali metal salt is within the polymer chain. A further preferred embodiment of the foregoing complex is where the therapeutic agent is selected from the group consisting of LHRH, somatostatin, bombesin/GRP, calcitonin, bradykinins, galanin, MSH, GRF, amylin, tachykinin, secretin, PTH, CGRP, neuromedin, pTHRP, glucagon, neurotensin, ACTH, PYY, and TSH, or analogues or fragments thereof. An even more preferred embodiment of the foregoing complex is where the therapeutic agent is a somatostatin analogue selected from the group consisting of H-β-D-Nal-Cys- Tyr-D-Trp-Lys-Val-Cys-Thr-NH$_2$, where the two Cys are bonded by a disulfide bond, N-hydroxyethylpiperazinyl-acetyl-D-Phe-Cys-Tyr-D-Trp-Lys-Abu-Cys-Thr-NH$_2$ where the two Cys are bonded by a disulfide bond or N-hydroxy-ethylpiperazinyl-ethylsulfonyl-Phe-Cys-Tyr-D-Trp-Lys-Abu-Cys-Thr-NH$_2$ where the two Cys are bonded by a disulfide bond or the therapeutic agent is an LHRH analogue of the formula p-Glu-His-Trp-Ser-Tyr-D-Trp-Leu-Arg-Pro-Gly-NH$_2$.

In still another aspect, the present invention provides a sustained release composition comprising any one of the complexes described hereinabove, wherein the sustained release composition is in the form of microparticles, microspheres or rods.

In a further aspect, the present invention provides a pharmaceutical composition comprising any one of the complexes or sustained release compositions having an effective amount of the therapeutic agent, described hereinabove and a pharmaceutically-acceptable carrier.

In a yet further aspect, the present invention provides a method of treating or preventing a disease or a condition, which comprises administering any of the pharmaceutical compositions described hereinabove to a patient in need thereof, wherein said disease or condition is a disease or condition that can be treated by the therapeutic agent in the pharmaceutical composition.

In a still further aspect, the present invention provides a method of administering any of the complexes or pharmaceutical compositions described hereinabove to a recipient, wherein the pharmaceutical composition or complex is administered orally, through the nasal passage, through the pulmonary passage or parenterally.

The word "peptide" as used herein encompasses oligopeptides, polypeptides and proteins.

The term "therapeutic agent" encompasses any chemical entity that can be used to treat a disease or condition in a patient in need thereof, and, thus, includes peptides. Preferably the therapeutic agent contains a cationic moiety or can be modified by a cationic moiety, which cationic moiety can be used to form a complex with a polymer of the present invention.

The polymers of the present invention are typically biodegradable agents, that is it disassociates in the biological environment to inert by-products, which are used to complex a therapeutic agent to make a sustained release formulation of the therapeutic agent. This complex, which may be formed into various pharmaceutically-acceptable compositions such as microspheres, microparticles or rods, optionally comprising a pharmaceutically-acceptable carrier, is typically used to provide a sustained delivery of the therapeutic agent to a recipient thereof over a period of time ranging from one day to thirty days.

DETAILED DESCRIPTION OF THE INVENTION

The lactone bearing biodegradable polymers of the invention are tailored to possess the desired chemical reactivity to provide controlled hydrolyzability and exhibit maximum binding capacity to a therapeutic agent having cationic groups, such as a peptide, by the selection of constituent monomers, co-monomers to form chains with predetermined compositions and molecular weights. A lactone bearing biodegradable polymer of this invention comprises a polymer selected from the group consisting of polyesters, polyorthoesters, polyphosphoesters, polycarbonates, polyanhydrides, polyphosphazenes polyoxalates, polyaminoacids, polyhydroxyalkanoates, polyethyleneglycol and copolymers and blends thereof, wherein the foregoing polymers can contain one or more of the following which may be present as polymers, prepolymers or copolymers: l-lactide, dl-lactide, ε-caprolactone, p-dioxanone, trimethylene carbonate, 1,5-dioxepan-2-one, 1,4-dioxepan-2-one, glycolide, ethylene glycol, propylene glycol, and/or butanediol.

The synthetic strategy employed to prepare compositions of the present invention comprise: synthesis of lactone bearing polymers; synthesis of ionic complexes between the lactone bearing polymer and the biologically active agent such as a peptide; and conversion of the ionic complexes to implants, rods, microspheres or microparticles, which are capable of slowly releasing the therapeutic agent in vivo.

Synthesis of lactone bearing polyesters: The lactone bearing polyesters can be synthesized by ring opening polymerization using a hydroxy or amino group present on a non-polymerizable lactone such as butyrolactone. Examples of non-polymerizable five membered lactones having at least one or more active hydrogen containing compound include, but are not limited to hydroxy butyrolactone, aminobutyrolactone, isopropylidene ribonolactone, mannarodilactone, sacharrodilactone, erythyronolactone, and the like. The functional group in these non-polymerizable lactone can be used to regulate the ring opening polymerization of monomers or mixtures of monomers such as glycolide, lactide, caprolactone, valerolactone, cyclic carbonates, cyclic anhydrides, oxalates, and the like.

Scheme 1

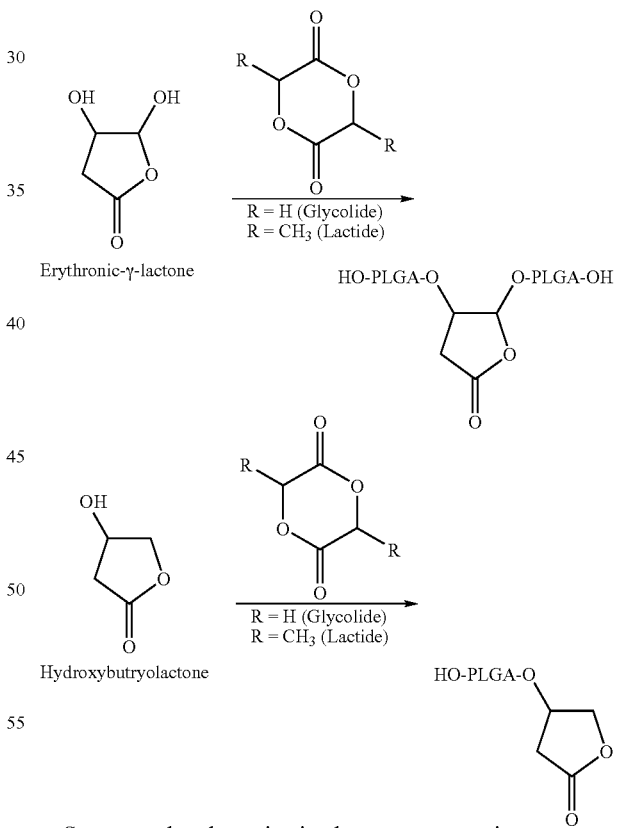

Step growth polymerization between appropriate amounts of dicarboxylic acid present on a non-polymerizable five-membered lactone and diol, to obtain (α,ω) dihydroxy oligoester containing non-polymerizable lactone ring could also be used. The dihydroxy functionalities on the oligoester can be used to grow polymer chains to produce high molecular weight polyester, containing non-polymerizable lactone rings.

Scheme 2

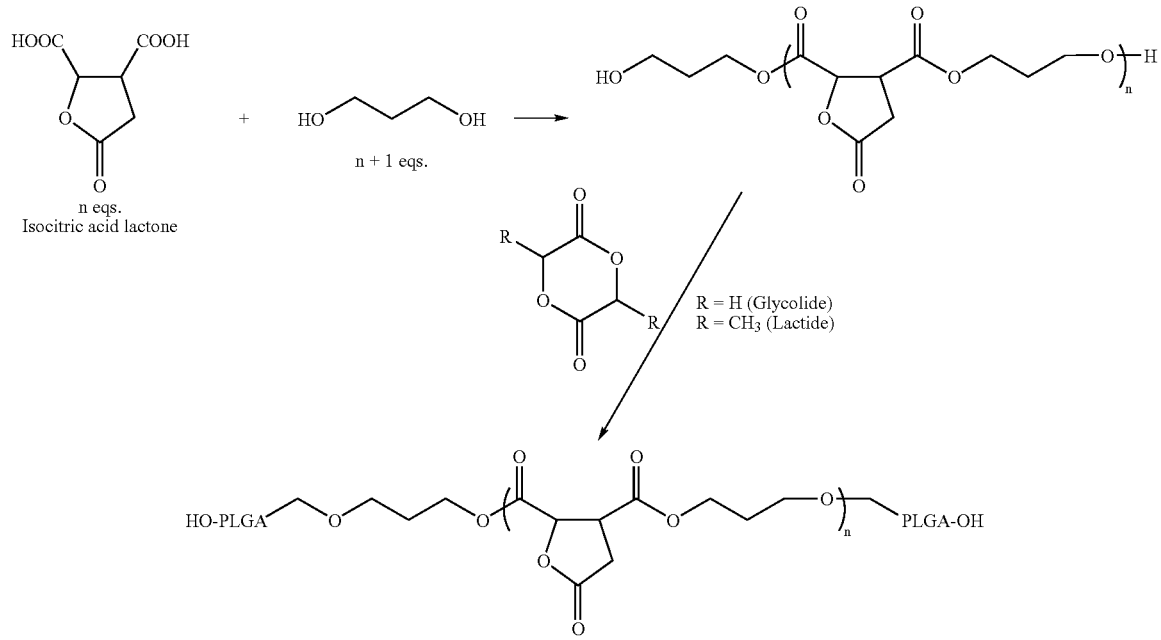

Ring opening polymerization of a lactone or a lactone mixture in the presence of a predetermined concentration of hydroxy or amino groups present on a non-polymerizable lactone as a chain initiator and a catalytic amount of organometallic catalyst, e.g., a mixture of dl-lactide, glycolide and hydroxy butyrolactone, are weighed into a glass reactor in an oxygen free nitrogen filled dry box. Stannous octoate catalyst is added as a solution in toluene. Vacuum is applied to remove the toluene and the reactor is filled with dry argon and left at a positive pressure of argon. The reaction vessel is immersed in an oil bath at a suitable temperature between 120–200° C. for polymerization for several hours. At the conclusion of the reaction, vacuum is applied to remove any residual monomer. The reaction vessel is cooled to room temperature and product is collected. The polymer obtained is further purified by dissolving in acetone, and precipitating in ten fold excess cold water. The precipitated polymer is collected by filtration. The product is dried under vacuum at 35° C.

The step growth polymerization which leads to ($\alpha,\omega$)-dihydroxy terminated oligoester containing non-polymerization lactone ring is performed by reacting appropriate amounts of a dicarboxylic acid functionalized lactone and diol, either at room temperature in the presence of coupling agents used in peptide chemistry such as N,N'-dicyclohexylcarbodiimide, N-hydroxybenzotriazole, 2-(1H-benzotriazole-1-yl)-1,1,3,3,-tetramethyluronium hexafluoro-phosphate, benzotriazole-1-yl-oxy-tris(dimethylamino)-phosphoniumhexafluorophosphate) or at high temperature wherein the water formed in the reaction is removed by azeotropization with a suitable organic solvent such as benzene, toluene or under a current of $N_2$ gas.

The simplest and the most versatile carboxylic functionalized five membered lactone is isocitric acid lactone, a Kreb's acid which would be metabolized in vivo. Examples of diols include simple diols as ethylene glycol, propylene glycol, butanediol, and ($\alpha,\omega$)-dihydroxy terminated oligomers or polymers such as polyethylene glycol, polypropylene glycol, polycaprolactone, polylactides, polyglycolides, polyanhydrides, polyorthoesters, or copolymers thereof. Or a diol may contain non-polymerizable five membered lactone, which may be polycondensed with a dicarboxylic acid. Examples of diols containing non-polymerizable lactones include but are not limited to mannarolactone, erythrynolactone, and the like. Dicarboxylic acids such as adipic, maleic, fumaric, glutaric, tartaric and the like may be used for polycondensation. The polycondensation may be optionally carried out in organic solvents such as dichloromethane, chloroform, tetrahydrofuran, dioxane, dimethylformamide, acetonitrile, dimethylsulfoxide, and the like in the presence of catalysts such as carbodiimide, benzotriazole, thionyl chloride, which are known in the art.

The product of the step growth polymerization may be obtained as a viscous liquid which gels on contact with water, depending on its hydrophilic-lipophilic balance (HLB value). It may be obtained as an amorphous powder by either driving the reaction to completion or by attaching polymer moieties by ring opening polymerization of lactides, glycolides, cyclic carbonates, cyclic anhydrides and the like, used as a mixture or individually to attain the desired properties. The molecular weight of the final polymer can be controlled by choosing the appropriate amount of prepolymer to the monomer. The polymer composition can also be tailored for a desired release profile of the therapeutic agent by appropriate choice of the monomers and molecular weight of the polymer.

Synthesis of a lactone bearing polymer of the instant invention comprising polyorthoesters can be realized according to the following scheme and substantially according to the procedures taught in Biomaterials, 19 (1998), 791–800, the contents of which are incorporated herein by reference.

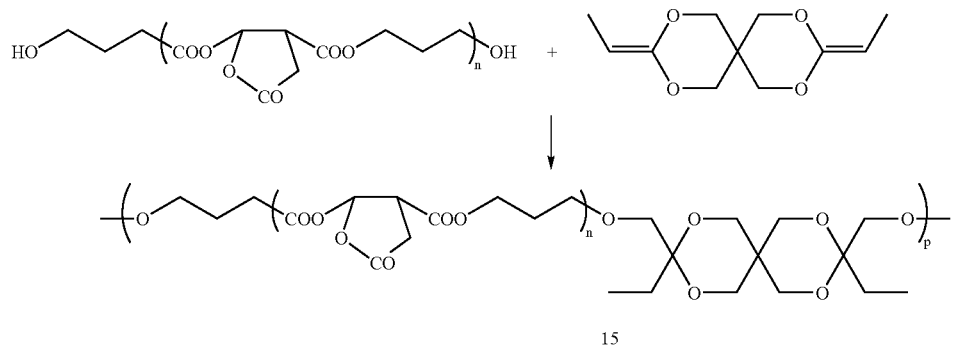

Synthesis of a lactone bearing polymer comprising polyphoesters can be accomplished by following the reaction scheme described below, and substantially according to the procedure described in U.S. Pat. No. 5,256,765, the contents of which are incorporated herein by reference, using a lactone bearing polymer in place of the polymer described therein.

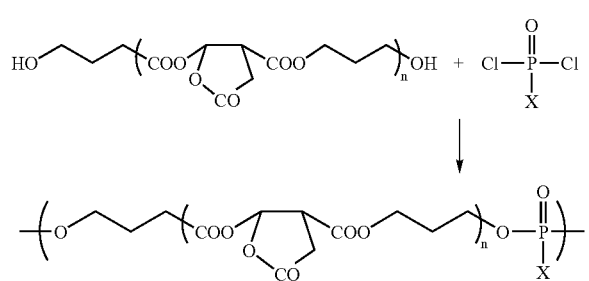

A lactone bearing polymer comprising polyphosphazenes can be synthesized by the reaction between poly(dichlorophosphazene) and aminobutyrolactone, and substantially according to the procedure described in Chapter 9 of the Handbook of Biodegradable Polymers, edited by A. J. Domb, J. Kost and D. M. Wiseman, Hardwood Academic Publishers, the contents of which are incorporated herein by reference, using a lactone-bearing polymer in place of the polymer described therein.

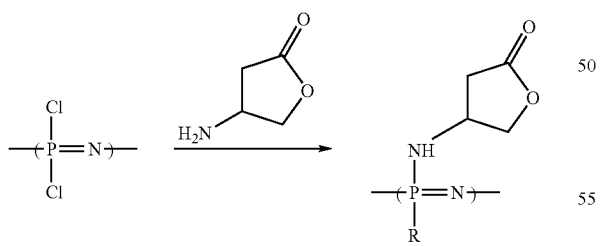

The polymer molecular weight determination is done by Gel Permeation Chromatography (GPC). The system consists of a Waters 6000A solvent delivery system (Waters Corporation, 26 Maple St., Milford, Mass. 01757), Dynamax Model Al-3 autoinjector (Ranin, Woburn, Mass.), Jordi Gel DVB Mixed bed (50×1 cm) column (Jordi Associates, Bellingham, Mass.) kept at a constant temperature using an Eppendorf CH-460 column heater (Madison, Wis.), Shimadzu RID-6A detector (Columbia, Md.). The data is acquired using a Viscotek Data Manager DM-400 and Viscotek Trisec Software (Viscotek Corporation, Houston, Tex.). The molecular weights are calculated in comparison to a calibration curve constructed using Polystyrene molecular standards purchased from PolySciences, Inc., Warrington, Pa.

Synthesis of Polymer/Peptide Ionic Complexes from Lactone Bearing Polymer and Cationic Therapeutic Agent:

All of the above lactone bearing polymers can be used to prepare ionic complexes with therapeutic agents, such as a peptide, having a cationic moiety. The lactone ring(s) present in these polymers can be opened by an alkali hydroxide to form alkali metal salt of the corresponding hydroxycarboxylic acid. In the case of γ-hydroxycarboxylic acid, it is known that the γ-hydroxycarboxylic acid always reverts back to the more thermodynamically favorable γ-lactone. Therefore, the presence of carboxylic groups in the latent lactone form does not enhance the acidic microenvironment within the polymer. A free acidic group can contribute towards the accelerated degradation of both the polyester and the polypeptide.

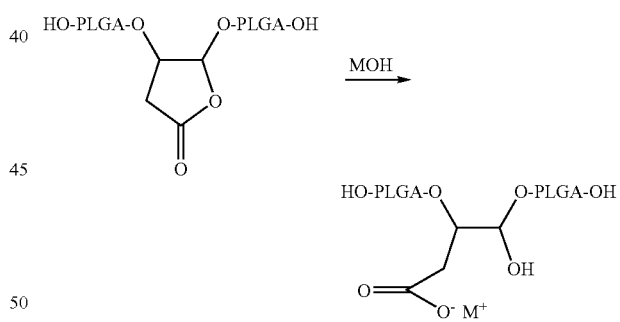

Examples of the physiologically active peptides that can form a complex with a lactone bearing polymer of the present invention include luteinizing hormone-releasing hormone (sometimes referred to as LHRH, gonadotropin-releasing hormone or Gn-RH), insulin, somatostatin, somatostatin derivative (Sandostatin®; see U.S. Pat. Nos. 4,087,390, 4,093,574, 4,100,117 and 4,253,998; Lanreotide®; see U.S. Pat. No. 4,853,371), growth hormones (GH), growth hormone-releasing hormones (GH-RH), prolactin, erythropoietin (EPO), adrenocorticotropic hormone (ACTH), ACTH derivatives (e.g., ebiratide), melanocyte-stimulating hormone (MSH), thyrotropin-releasing hormone (represented by the structural formula (Pyr)Glu-His-ProNH$_2$, hereinafter also referred to as TRH) and salts and derivatives thereof (see Japanese Patent Unexamined Publication Nos.

121273/1975 and 116465/1977), thyroid-stimulating hormone (TSH), luteinizing hormone (LH), follicle-stimulating hormone (FSH), vasopressin, vasopressin derivative (desmopressin (see Folia Endocrinologica Japonica, Vol. 54, No. 5, pp. 676–691 (1978), oxytocin, calcitonin, glucagon, gastrin, secretin, pancreozymin, cholecystokinin, angiotensin, human placental lactogen, human chorionic gonadotropin (HCG), enkephalin, enkephalin derivatives (see U.S. Pat. No. 4,277,394 and European Patent Publication No. 31567), endorphin, kyotorphin, interferons (e.g., $\alpha$-, $\beta$- and $\gamma$-interferons), interleukins (e.g., interleukin 1, 2, 3, 4, 5, 6, 7, 8, 9, 10, 11 and 12) tuftsin, thymopoietin, thymosin, thymostimulin, thymic humoral factor (THF), blood thymic factor (FTS) and derivatives thereof (see U.S. Pat. No. 4,229,438), tumor necrosis factor (TNF), colony-stimulating factors (e.g., CSF, GCSF, GMCSF, MCSF), motilin, dynorphin, bombesin, neurotensin, caerulein, bradykinin, atrium sodium-excretion increasing factor, nerve growth factor (NGF), cell growth factors (e.g., EGF, TGF-$\alpha$, TGF-$\beta$, PDGF, acidic FGF, basic FGF), nerve nutrition factors (e.g., NT-3, NT-4, CNTF, GDNF, BDNF), and endothelin-antagonistic peptides and their analogs (see European Patent Publication Nos. 436189, 457195 and 496452, and Japanese Patent Unexamined Publication Nos. 94692/1991 and 130299/1991), a protein derived from $\alpha$ 1 domain of major histocompatibility class I antigen complex (Proceedings of the National Academy of Sciences of the Untied States of America, vol. 91, 9086–9090 (1994) and vol. 94, 11692–11697 (1997)) which has an activity of inhibiting an internalization of insulin receptor, insulin-like growth factor (IGF)-1 receptor, IGF-2 receptor, transferrin receptor, epidermal growth factor receptor, low density lipoprotein (LDL) receptor, macrophage scavenger receptor, GLUT-4 transporter, growth hormone receptor and leptin receptor, and their analogs (derivatives), furthermore their fragments or derivatives thereof.

When the physiologically active peptides are salts, the salts include pharmacologically acceptable salts. Examples of the salts are salts formed with inorganic acids (e.g., hydrochloric acid, sulfuric acid, nitric acid and boric acid) or salts formed with organic acids (e.g., carbonic acid, bicarbonic acid, succinic acid, acetic acid, propionic acid and trifluoroacetic acid), when the physiologically active peptide has a basic group such as the amino group.

Examples of specific LHRH analogues that can form a complex with a lactone bearing polymer of the present invention include tryptorelin (p-Glu-His-Trp-Ser-Tyr-D-Trp-Leu-Arg-Pro-Gly-NH$_2$), buserelin ([D-Ser(t-Bu)$^6$, des-Gly-NH$_2{}^{10}$]-LHRH(1–9)NHEt), deslorelin ([D-Trp$^6$, des-Gly-NH$_2{}^{10}$]-LHRH(1–9)NHEt, fertirelin ([des-Gly-NH$_2{}^{10}$]-LHRH(1–9)NHEt), gosrelin ([D-Ser(t-Bu)$^6$, Azgly$^{10}$]-LHRH), histrelin ([D-His(Bzl)$^6$, des-Gly-NH$_2{}^{10}$]-LHRH (1–9)NHEt), leuprorelin ([D-Leu6, des-Gly-NH$_2{}^{10}$]-LHRH (1–9)NHEt), lutrelin ([D-Trp$^6$, MeLeu$^7$, des-Gly-NH$_2{}^{10}$]-LHRH (1–9)NHEt), nafarelin ([D-Nal$^6$]-LHRH and pharmaceutically acceptable salts thereof.

Preferred somatostatin analogs that can form a complex with a lactone bearing polymer of the present invention include those covered by formulae or those specifically recited in the publications set forth below, all of which are incorporated herein by reference:

Van Binst, G. et al. Peptide Research 5:8 (1992);
Horvath, A. et al. Abstract, "Conformations of Somatostatin Analogs Having Antitumor Activity", 22nd European peptide Symposium, Sep. 13–19, 1992, Interlaken, Switzerland;
PCT Application WO 91/09056 (1991);
EP Application 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987)
U.S. Pat. No. 4,650,787 (1987);
U.S. Pat. No. 4,603,120 (1986);
U.S. Pat. No. 4,585,755 (1986);
EP Application 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,190 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);
PCT Application No. WO 90/12811 (1990);
PCT Application No. WO 97/01579 (1997);
PCT Application No. WO 91/18016 (1991);
U.K. Application No. GB 2,095,261 (1981); and
French Application No. FR 2,522,655 (1983).

Examples of somatostatin analogs that can form a complex with a lactone bearing polymer of the present invention include, but are not limited to, the following somatostatin analogs which are disclosed in the above-cited references:

H-D-$\beta$-Nal-Cys-Tyr-D-Trp-Lys-Thr-Cys-Thr-NH$_2$;
H-D-Phe-Cys-Phe-D-Trp-Lys-Thr-Cys-$\beta$-Nal-NH$_2$;
H-D-Phe-Cys-Tyr-D-Trp-Lys-Thr-Cys-$\beta$Nal-NH$_2$;
H-D-$\beta$-Nal-Cys-Phe-D-Trp-Lys-Thr-Cys-Thr-NH$_2$;
H-D-Phe-Cys-Tyr-D-Trp-Lys-Thr-Pen-Thr-NH$_2$;
H-D-Phe-Cys-Phe-D-Trp-Lys-Thr-Pen-Thr-NH$_2$;
H-D-Phe-Cys-Tyr-D-Trp-Lys-Thr-Pen-Thr-OH;
H-D-Phe-Cys-Phe-D-Trp-Lys-Thr-Pen-Thr-OH;
H-Gly-Pen-Phe-D-Trp-Lys-Thr-Cys-Thr-OH;
H-Phe-Pen-Tyr-D-Trp-Lys-Thr-Cys-Thr-OH;
H-Phe-Pen-Phe-D-Trp-Lys-Thr-Pen-Thr-OH;
H-D-Phe-Cys-Phe-D-Trp-Lys-Thr-Cys-Thr-ol;
H-D-Phe-Cys-Phe-D-Trp-Lys-Thr-Cys-Thr-NH$_2$;
H-D-Trp-Cys-Tyr-D-Trp-Lys-Val-Cys-Thr-NH$_2$;
H-D-Trp-Cys-Phe-D-Trp-Lys-Thr-Cys-Thr-NH$_2$;

H-D-Phe-Cys-Tyr-D-Trp-Lys-Val-Cys-Thr-NH$_2$;
H-D-Phe-Cys-Tyr-D-Trp-Lys-Val-Cys-Trp-NH$_2$;
H-D-Phe-Cys-Tyr-D-Trp-Lys-Val-Cys-Thr-NH$_2$;
Ac-D-Phe-Lys*-Tyr-D-Trp-Lys-Val-Asp*-Thr-NH$_2$ (an amide bridge formed between Lys* and Asp*);
Ac-hArg(Et)$_2$-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NH$_2$;
Ac-D-hArg(Bu)-Gly-Cys-Phe-D-Trp-Lys-Thr-Cys-Thr-NH$_2$;
Ac-D-hArg(Et)$_2$-Cys-Phe-D-Trp-Lys-Thr-Cys-Thr-NH$_2$;
Ac-L-hArg(Et)$_2$-Cys-Phe-D-Trp-Lys-Thr-Cys-Thr-NH$_2$;
Ac-D-hArg(CH$_2$CF$_3$)$_2$-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Phe-NH$_2$;
Ac-D-hArg(CH$_2$CF$_3$)$_2$-Gly-Cys-Phe-D-Trp-Lys-Thr-Cys-Thr-NHEt;
Ac-L-hArg(CH$_2$-CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys(Me)-Thr-Cys-Thr-NH$_2$;
Ac-D-hArg(CH$_2$CF$_3$)$_2$-Gly-Cys-Phe-D-Trp-Lys(Me)-Thr-Cys-Thr-NHEt;
Ac-hArg(CH$_3$, hexyl)-Gly-Cys-Phe-D-Trp-Lys-Thr-Cys-Thr-NH$_2$;
H-hArg(hexyt$_2$)-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NHEt;
Ac-D-hArg(Et)$_2$-Gly-Cys-Phe-D-Trp-Lys-Thr-Cys-Phe-NH$_2$;
Propionyl-D-hArg(Et)$_2$-Gly-Cys-Phe-D-Trp-Lys(iPr)-Thr-Cys-Thr-N H$_2$;
Ac-D-β-Nal-Gly-Cys-Phe-D-Trp-Lys-Thr-Cys-Gly-hArg (Et)$_2$—NH$_2$;
Ac-D-Lys(iPr)-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Phe-NH$_2$;
Ac-D-hArg(Et)$_2$-D-hArg(Et)$_2$-Gly-Cys-Phe-D-Trp-Lys-Thr-Cys-Thr-NH$_2$;
Ac-Cys-Lys-Asn-4-Cl-Phe-Phe-D-Trp-Lys-Thr-Phe-Thr-Ser-D-Cys-NH$_2$;
H-Bmp-Tyr-D-Trp-Lys-Val-Cys-Thr-NH$_2$;
H-Bmp-Tyr-D-Trp-Lys-Val-Cys-Phe-NH$_2$;
H-Bmp-Tyr-D-Trp-Lys-Val-Cys-p-Cl-Phe-NH$_2$;
H-Bmp-Tyr-D-Trp-Lys-Val-Cys-β-Nal-NH$_2$;
H-D-β-Nal-Cys-Tyr-D-Trp-Lys-Val-Cys-Thr-NH$_2$;
H-D-Phe-Cys-Tyr-D-Trp-Lys-Abu-Cys-Thr-NH$_2$;
H-D-Phe-Cys-Tyr-D-Trp-Lys-Abu-Cys-β-Nal-NH$_2$;
H-pentafluoro-D-Phe-Cys-Tyr-D-Trp-Lys-Val-Cys-Thr-NH$_2$;
Ac-D-β-Nal-Cys-pentafluoro-Phe-D-Trp-Lys-Val-Cys-Thr-NH$_2$;
H-D-β-Nal-Cys-Tyr-D-Trp-Lys-Val-Cys-β-Nal-NH$_2$;
H-D-Phe-Cys-Tyr-D-Trp-Lys-Val-Cys-β-Nal-NH$_2$;
H-D-β-Nal-Cys-Tyr-D-Trp-Lys-Abu-Cys-Thr-NH$_2$;
H-D-p-Cl-Phe-Cys-Tyr-D-Trp-Lys-Abu-Cys-Thr-NH$_2$;
Ac-D-p-Cl-Phe-Cys-Tyr-D-Trp-Lys-Abu-Cys-Thr-NH$_2$;
H-D-β-Nal-D-Trp-Lys-Val-Cys-Thr-NH$_2$;
H-D-Phe-Cys-Tyr-D-Trp-Lys-Cys-Thr-NH$_2$;
cyclo(Pro-Phe-D-Trp-N-Me-Lys-Thr-Phe);
cyclo(Pro-Phe-D-Trp-N-Me-Lys-Thr-Phe);
cyclo(Pro-Phe-D-Trp-Lys-Thr-N-Me-Phe);
cyclo(N-Me-Ala-Tyr-D-Trp-Lys-Thr-Phe);
cyclo(Pro-Tyr-D-Trp-Lys-Thr-Phe);
cyclo(Pro-Phe-D-Trp-Lys-Thr-Phe);
cyclo(Pro-Phe-L-Trp-Lys-Thr-Phe);
cyclo(Pro-Phe-D-Trp(F)-Lys-Thr-Phe);
cyclo(Pro-Phe-Trp(F)-Lys-Thr-Phe);
cyclo(Pro-Phe-D-Trp-Lys-Ser-Phe);
cyclo(Pro-Phe-D-Trp-Lys-Thr-p-Cl-Phe);
cyclo(D-Ala-N-Me-D-Phe-D-Thr-D-Lys-Trp-D-Phe);
cyclo(D-Ala-N-Me-D-Phe-D-Val-Lys-D-Trp-D-Phe);
cyclo(D-Ala-N-Me-D-Phe-D-Thr-Lys-D-Trp-D-Phe);
cyclo(D-Abu-N-Me-D-Phe-D-Val-Lys-D-Trp-D-Tyr);
cyclo(Pro-Tyr-D-Trp-t-4-AchxAla-Thr-Phe);
cyclo(Pro-Phe-D-Trp-t-4-AchxAla-Thr-Phe);
cyclo(N-Me-Ala-Tyr-D-Trp-Lys-Val-Phe);
cyclo(N-Me-Ala-Tyr-D-Trp-t-4-AchxAla-Thr-Phe);
cyclo(Pro-Tyr-D-Trp-4-Amphe-Thr-Phe);
cyclo(Pro-Phe-D-Trp-4-Amphe-Thr-Phe);
cyclo(N-Me-Ala-Tyr-D-Trp-4-Amphe-Thr-Phe);
cyclo(Asn-Phe-Phe-D-Trp-Lys-Thr-Phe-Gaba);
cyclo(Asn-Phe-Phe-D-Trp-Lys-Thr-Phe-Gaba-Gaba);
cyclo(Asn-Phe-D-Trp-Lys-Thr-Phe);
cyclo(Asn-Phe-Phe-D-Trp-Lys-Thr-Phe-NH(CH$_2$)$_4$CO);
cyclo(Asn-Phe-Phe-D-Trp-Lys-Thr-Phe-β-Ala);
cyclo(Asn-Phe-Phe-D-Trp-Lys-Thr-Phe-D-Glu)-OH;
cyclo(Phe-Phe-D-Trp-Lys-Thr-Phe);
cyclo(Phe-Phe-D-Trp-Lys-Thr-Phe-Gly);
cyclo(Phe-Phe-D-Trp-Lys-Thr-Phe-Gaba);
cyclo(Asn-Phe-Phe-D-Trp-Lys-Thr-Phe-Gly);
cyclo(Asn-Phe-Phe-D-Trp(F)-Lys-Thr-Phe-Gaba);
cyclo(Asn-Phe-Phe-D-Trp(NO$_2$)-Lys-Thr-Phe-Gaba);
cyclo(Asn-Phe-Phe-Trp(Br)-Lys-Thr-Phe-Gaba);
cyclo(Asn-Phe-Phe-D-Trp-Lys-Thr-Phe(I)-Gaba);
cyclo(Asn-Phe-Phe-D-Trp-Lys-Thr-Tyr(But)-Gaba);
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Pro-Cys)-OH;
cyclo(Bmp-Lys-Asn-Phe-Phe-D-Trp-Lys-Thr-Phe-Thr-Tpo-Cys)-OH;
cyclo(Bmp-Lys-Asn-Phe-Phe-D-Trp-Lys-Thr-Phe-Thr-Me-Leu-Cys)-OH;
cyclo(Phe-Phe-D-Trp-Lys-Thr-Phe-Phe-Gaba);
cyclo(Phe-Phe-D-Trp-Lys-Thr-Phe-D-Phe-Gaba);
cyclo(Phe-Phe-D-Trp(5F)-Lys-Thr-Phe-Phe-Gaba);
cyclo(Asn-Phe-Phe-D-Trp-Lys(Ac)-Thr-Phe-NH—(CH$_2$)$_3$—CO);
cyclo(Lys-Phe-Phe-D-Trp-Lys-Thr-Phe-Gaba);
cyclo(Lys-Phe-Phe-D-Trp-Lys-Thr-Phe-Gaba);
cyclo(Orn-Phe-Phe-D-Trp-Lys-Thr-Phe-Gaba);
H-Cys-Phe-Phe-D-Trp-Lys-Thr-Phe-Cys-NH$_2$;
H-Cys-Phe-Phe-D-Trp-Lys-Ser-Phe-Cys-NH$_2$;
H-Cys-Phe-Tyr-D-Trp-Lys-Thr-Phe-Cys-NH$_2$; and
H-Cys-Phe-Tyr(I)-D-Trp-Lys-Thr-Phe-Cys-NH$_2$.

A disulfide bridge is formed between the two free thiols (e.g., Cys, Pen, or Bmp residues) when they are present in a peptide; however, the disulfide bond is not shown.

Also included are somatostatin agonists of the following formula:

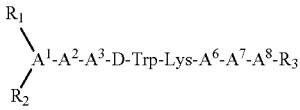

wherein

A$^1$ is a D- or L-isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe, wherein X is CH$_3$, Cl, Br, F, OH, OCH$_3$ or NO$_2$;

A$^2$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

A$^3$ is pyridyl-Ala, Trp, Phe, β-Nal, 2,4-dichloro-Phe, pentafluoro-Phe, o-X-Phe, or p-X-Phe, wherein X is CH$_3$, Cl, Br, F, OH, OCH$_3$ or NO$_2$;

A$^6$ is Val, Ala, Leu, Ile, Nle, Thr, Abu, or Ser;

A$^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

A$^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is CH$_3$, Cl, Br, F, OH, OCH$_3$ or NO$_2$;

each R$_1$ and R$_2$, independently, is H, lower acyl or lower alkyl; and R$_3$ is OH or NH$_2$; provided that at least one of A$^1$ and A$^8$ and one of A$^2$ and A$^7$ must be an aromatic amino acid; and further provided that A$^1$, A$^2$, A$^7$ and A$^8$ cannot all be aromatic amino acids.

Examples of linear agonists that can form a complex with a lactone bearing polymer of the present invention include:

H-D-Phe-p-chloro-Phe-Tyr-D-Trp-Lys-Thr-Phe-Thr-NH$_2$;
H-D-Phe-p-NO$_2$-Phe-Tyr-D-Trp-Lys-Val-Phe-Thr-NH$_2$;
H-D-Nal-p-chloro-Phe-Tyr-D-Trp-Lys-Val-Phe-Thr-NH$_2$;
H-D-Phe-Phe-Phe-D-Trp-Lys-Thr-Phe-Thr-NH$_2$;
H-D-Phe-Phe-Tyr-D-Trp-Lys-Val-Phe-Thr-NH$_2$;
H-D-Phe-p-chloro-Phe-Tyr-D-Trp-Lys-Val-Phe-Thr-NH$_2$; and
H-D-Phe-Ala-Tyr-D-Trp-Lys-Val-Ala-βD-Nal-NH$_2$.

If desired, one or more chemical moieties, e.g., a sugar derivative, mono or poly-hydroxy C$_{2-12}$ alkyl, mono or poly-hydroxy C$_{2-12}$ acyl groups, or a piperazine derivative, can be attached to the somatostatin agonist, e.g., to the N-terminus amino acid. See PCT Application WO 88/02756, European Application 0 329 295, and PCT Application No. WO 94/04752. An example of somatostatin agonists which contain N-terminal chemical substitutions are:

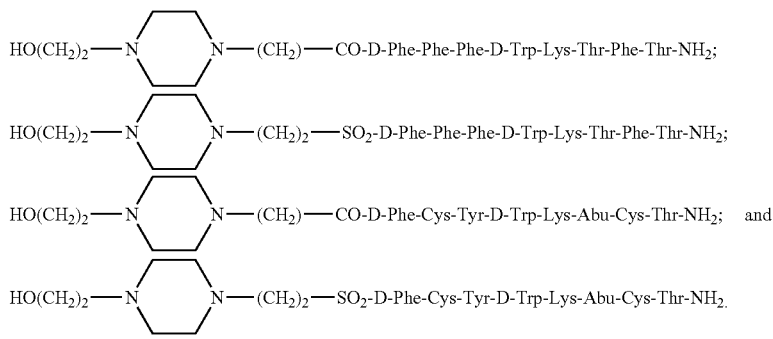

The formation of the ionic complexes is achieved by direct molecular interaction of the components (lactone bearing polymer and therapeutic agent, such as a peptide) in an appropriate solvent with a pretreatment of the lactone bearing polymer with an inorganic base which results in the ring-opened hydroxycarboxylic acid corresponding to the lactone bearing polymer. The lactone bearing polymer is dissolved in a suitable aprotic solvent in a concentration range of 2–25% (w/v). These organic solvents are either partially or completely miscible with water. Such solvents include acetone, tetrahydrofuran, acetonitrile, ethylene glycol, dimethyl ether, methyl formate, dioxane and the like. To this polymer solution, an aqueous solution of a base such as sodium, potassium or ammonium, calcium, hydroxide or carbonate or bicarbonate, is added to open the intact five membered cyclic lactone, to yield the corresponding metallic salts of hydroxycarboxylic acid. In general, the amount of the inorganic base used corresponds to the amount of counter-anion of the basic peptide.

The mixture of the metallic salts of hydroxycarboxylic acid polymer and the inorganic base are stirred and a solution of the therapeutic agent, such as a peptide, in a minimum amount of water either alone or in combination with the same organic solvent used for dissolving the peptide, is added. The amount of organic solvent to aqueous in the mixture is adjusted to get a clear solution which is left stirring for 1–2 hours. This solution is precipitated in ice cold water. The precipitate formed is collected by vacuum filtration and dried under vacuum. The peptide content in the formulation is determined by nitrogen analysis performed by QTI, Whitehouse, N.J.

Conversion of ionic complexes to implants, rods, microspheres or microparticles:

The polymer-peptide ionic complexes of this invention can be converted to injectable dosage forms such as implants, rods, microspheres or microparticles by any of the relevant methods described in PCT International Publication Number WO 97/39738, the contents of which are incorporated herein by reference.

The pharmaceutical compositions of this invention can be administered to a patient via administration routes well known to those of ordinary skill in the art, such as parenteral administration, oral administration or topical administration. Preferably, it is administered as a powder or a suspension via intranasal route or as an inhalant through the pulmonary system. When it is administered parenterally it is preferable that it is administered as a dispersion in an isotonic aqueous medium or in a non-aqueous, absorbable gel-forming liquid polyester as described in U.S. Pat. No. 5,612,052, the contents of which are incorporated herein by reference. The formulations comprising microparticles of the present invention can also include a variety of optional components. Such components include, but are not limited to, surfactants, viscosity controlling agents, medicinal agents, cell growth modulators, dyes, complexing agents, antioxidants, other polymers such as carboxymethyl cellulose, gums such as guar gum, waxes/oils such as castor oil, glycerol, dibutyl phthalate and di(2-ethylhexyl)phthalate as well as many others. If used, such optional components comprise form about 0.1% to about 20%, preferably from about 0.5% to about 5% of the total formulation.

Compositions or formulations of this invention can be used to treat a disease or condition in a patient in need thereof according to the use that is known for the therapeutic agent, such as a peptide or peptides, which is in the composition, which are known to one of ordinary skill in the art. For example, microparticles of the present invention comprising a somatostatin analogue will be useful in treating a disease or condition that can be treated with somatostatin or an analogue thereof.

The effective dosages of a composition or formulation of the present invention to be administered to a patient can be determined by the attending physician or veterinarian and will be dependent upon the proper dosages contemplated for the therapeutic agent and the quantity of the therapeutic agent in the composition. Such dosages will either be known or can be determined by one of ordinary skill in the art without undue experimentation.

The following examples illustrate the present invention and are not to be construed to limit the scope of the present invention.

EXAMPLE 1

Ring Opening Polymerization: Synthesis of 65/35 p(dl-lactide-co-glycolide) Initiated by Erythrynolactone:

DL-Lactide (43.8 g, 0.3041M), glycolide (17.6 g, 1517M), erythrynolactone (1 g, 0.0084M) and 0.2 ml stannous octoate catalyst were added to the reaction vessel provided with a mechanical stirrer. The reaction vessel was evacuated and purged with dry argon at least three times and then left at a positive pressure of argon. The reaction vessel was immersed in an oil bath kept at about 160° C. The reaction was allowed to proceed for about 6 hours. After completion of the reaction, the temperature was lowered to about 100° C. and the vessel was evacuated to remove any residual monomer. The reaction vessel was cooled to room temperature, quenched in liquid $N_2$ and the polymer was collected. The polymer was further purified by preparing a 10% solution and precipitating in cold water. The precipitate was collected and dried under vacuum. Polymer molecular weight determined by GPC analysis is Mn=7250, Mw=12700

EXAMPLE 2

Ring Opening Polymerization: Synthesis of p(dl-Lactide) Initiated by Isopropylidene Ribonolactone:

DL-Lactide (60 g, 0.4166M) and isopropylidene ribonolactone (2.35 g, 0.0125M) were polymerized according to the procedure described in Example 1. The molecular weights of the polymer obtained determined by GPC analysis is Mn=5050, Mw=7980.

EXAMPLE 3

Step Growth Polymerization and Subsequent Ring Opening Polymerization: Preparation of polyethylene glycol-co-poly(lactide-co-glycolide) copolymers Containing Butrylolactone Isocitric acid (Aldrich Chemicals, St. Louis, Mo.) (2.5 g, 0.0143M) and polyethylene glycol-400 were mixed in a three necked round bottom flask, along with 50 ml of toluene. The toluene was refluxed at about 130° C. to azeotropically remove the water formed during the reaction by using a Dean-Stark apparatus. After about 48 h, the toluene was completely removed by distillation, and DL-lactide (30 g, 0.2082M), and glycolide (16.1 g, 0.1388M) were added along with 0.2 ml stannous octoate catalyst in toluene. The temperature of the reaction vessel was raised to about 160° C. and the polymerization was carried out for about 6 h. At the end of the polymerization, the reaction vessel was evacuated to remove any residual monomer.

EXAMPLE 4

Step Growth Polymerization and Subsequent Ring Opening Polymerization:

Isocitric acid lactone (2.5 g, 0.0143M) and propanediol (1.202 g, 0.0157M) were mixed and reacted at about 90° C., under refluxing benzene. The water formed was removed by azeotropization with a Dean-Stark trap. The reaction was allowed to proceed overnight, after which benzene was removed by distillation to yield a viscous liquid which solidifies on cooling.

The reaction vessel was transferred to a dry-box and 25.2 g of dl-lactide and 7.25 g of glycolide were added along with 0.2 ml stannous octoate solution in toluene. The reaction vessel was purged with dry argon and the polymerization was performed at about 160° C. for about 8 h. The polymer was quenched in liquid $N_2$, collected and dissolved in acetone and precipitated in cold water. The filtered polymer was dried under vacuum at about 40° C. Mn=3790, Mw=7040, as determined by GPC.

EXAMPLE 5

Synthesis of Ionic Complexes of Polymer Synthesized in Example 4 and Lanreotide® using 1N NaOH as the base:

One gram of polymer dissolved in acetone was treated with 0.45 ml 1N NaOH. The solution was stirred for about 20 min, and 0.29 g of Lanreotide® (Kinerton, Ltd., Dublin, Ireland; Lanreotide has the formula: H-β-D-Nal-Cys-Tyr-D-Trp-Lys-Val-Cys-Thr-$NH_2$ where the two Cys are bonded by a disulfide bond), dissolved in 2 ml of 1:1 acetone/water was added to the polymer solution. The polymer solution was left stirring for about 2 h, and then it was precipitated in cold water. The product was filtered and vacuum dried. The peptide content in the formulation determined by nitrogen analysis was 17.6%.

EXAMPLE 6

Synthesis of Ionic Complexes of the Polymer Synthesized in Example 4 and Lanreotide® using NaHCO₃ as the Base:

One gram of the polymer made in Example 4 dissolved in acetone was treated with 0.45 ml of 1N NaHCO₃. The solution was stirred for about 20 min, and 0.29 g of Lanreotide® dissolved in 2 ml of 1:1 acetone/water was added to the polymer solution. The polymer solution was left stirring for about 2 h, and it was precipitated in cold water. The product was filtered and vacuum dried. The peptide content in the formulation determined by nitrogen analysis was 17.6%.

EXAMPLE 7

In Vivo Testing of the Samples Prepared in Examples 5 and 6:

Samples from Examples 5 & 6 were each separately ground and sieved with a mortar and pestle, and sieved using a 125 micron sieve. Rats were administered 6.75 mg of peptide equivalent per rat, using an injection medium consisting of 2% carboxymethylcellulose, 1% Tween 20® (Aldrich Chemicals, St. Louis, Mo.) and saline. Blood samples were collected at various time intervals and the plasma Lanreotide® levels were determined by radioimmuno assay. The plasma Lanreotide® levels (ng/ml) for the two samples tested are shown in Table I below.

TABLE I

| Sample/Time | 6 h | Day 2 | Day 8 | Day 15 | Day 22 |
|---|---|---|---|---|---|
| Example 5 | 21.7 ± 4.5 | 30.3 ± 2.7 | 30.2 ± 7.5 | 0.8 ± 0.3 | 0.05 ± 0.02 |
| Example 6 | 24.4 ± 5.2 | 31.4 ± 5.8 | 20.8 ± 7.2 | 1.4 ± 1.2 | 0.141 ± 0.09 |

What is claimed is:

1. A complex comprising a polymer bearing non-polymerizable lactone ring wherein the polymer is selected from the group consisting of polyester, polyorthoester, polyphosphoester, polycarbonates, polyanhydrides and polyphosphazenes and copolymers and blends thereof, ionically complexed with a therapeutic agent containing at least one cationic group.

2. A complex comprising a polymer bearing non-polymerizable lactone ring wherein the polymer is a polyester selected from the group consisting of l-lactide, dl-lactide, glycolide, and polyethylene glycol and the non-polymerizable lactone ring is selected from the group consisting of hydroxybutyrolactone, erythrynolactone, isopropylidene ribonolactone, isocitric acid lactone, mannarolactone, sacharrodilactone and glucarodilactone, wherein the non-polymerizable lactone ring has been ring opened to its corresponding hydroxycarboxylic acid alkali metal salt, wherein the hydroxycarboxylic acid alkali metal salt is within the polymer chain, ionically complexed with a therapeutic agent containing at least one cationic group.

3. A complex according to claim 2, wherein the therapeutic agent is selected from the group consisting of LHRH, somatostatin, bombesin/GRP, calcitonin, bradykinins, galanin, MSH, GRF, amylin, tachykinin, secretin, PTH, CGRP, neuromedin, pTHRP, glucagon, neurotensin, ACTH, PYY, PYY, and TSH, or an analogue or fragment thereof.

4. A complex according to claim 3, wherein the therapeutic agent is a somatostatin analogue selected from the group consisting of H-β-D-Nal-Cys-Tyr-D-Trp-Lys-Val-Cys-Thr-NH2, where the two Cys are bonded by a disulfide bond, N-hydroxyethylpiperazinyl-acetyl-D-Phe-Cys-Tyr-D-Trp-Lys-Abu-Cys-Thr-NH2 where the two Cys are bonded by a disulfide bond or N-hydroxyethylpiperazinyl-ethylsulfonyl-Phe-Cys-Tyr-D-Trp-Lys-Abu-Cys-Thr-NH₂ where the two Cys are bonded by a disulfide bond.

5. A complex according to claim 3, wherein the therapeutic agent is an LHRH analogue of the formula p-Glu-His-Trp-Ser-Tyr-D-Trp-Leu-Arg-Pro-Gly-NH₂.

6. A sustained release composition comprising a complex according to claim 4 wherein the composition is in the form of microparticles, microspheres or rods.

7. A sustained release composition comprising a complex according to claim 5 wherein the composition is in the form of microparticles, microspheres or rods.

8. A pharmaceutical composition comprising a sustained release composition according to claim 6 having an effective amount of the therapeutic agent and a pharmaceutically-acceptable carrier.

9. A pharmaceutical composition comprising a sustained release composition according to claim 7 having an effective amount of the therapeutic agent and a pharmaceutically-acceptable carrier.

10. A method of treating or preventing a disease or a condition, which comprises administering a pharmaceutical composition according to claim 8 to a patient in need thereof, wherein said disease or condition is a disease or condition that can be treated by the therapeutic agent in the pharmaceutical composition.

11. A method of treating or preventing a disease or a condition, which comprises administering a pharmaceutical composition according to claim 9 to a patient in need thereof, wherein said disease or condition is a disease of condition that can be treated by the therapeutic agent in the pharmaceutical composition.

12. A method of administering a pharmaceutical composition according to claim 8 to a recipient, wherein said pharmaceutical composition is administered orally, through the nasal passage, through the pulmonary passage or parenterally.

13. A method of administering a pharmaceutical composition according to claim 9 to a recipient, wherein said pharmaceutical composition is administered orally, through the nasal passage, through the pulmonary passage or parenterally.

14. A complex according to claim 1, wherein said non-polymerizable lactone ring is a five-member lactone ring.

15. A complex according to claim 1, wherein said non-polymerizable lactone ring is a six-member lactone ring.

16. A complex according to claim 2, wherein said non-polymerizable lactone ring is a five-member lactone ring.

17. A complex according to claim 2, wherein said non-polymerizable lactone ring is a six-member lactone ring.

* * * * *